(12) United States Patent
Thorens (10) Patent No.: US 10,687,556 B2
(45) Date of Patent: Jun. 23, 2020

(54) BIOLOGICAL CONTROL IN ELECTRONIC SMOKING ARTICLES

(71) Applicant: PHILIP MORRIS PRODUCTS S.A., Neuchatel (CH)

(72) Inventor: Michel Thorens, Moudon (CH)

(73) Assignee: Philip Morris Products S.A., Neuchatel (CH)

(*) Notice: Subject to any disclaimer, the term of this patent is extended or adjusted under 35 U.S.C. 154(b) by 72 days.

(21) Appl. No.: 15/575,178

(22) PCT Filed: Jun. 9, 2016

(86) PCT No.: PCT/IB2016/053403
§ 371 (c)(1),
(2) Date: Nov. 17, 2017

(87) PCT Pub. No.: WO2016/199062
PCT Pub. Date: Dec. 15, 2016

(65) Prior Publication Data
US 2018/0140016 A1    May 24, 2018

(30) Foreign Application Priority Data

Jun. 12, 2015  (EP) .................................... 15171992

(51) Int. Cl.
*A24F 47/00*   (2020.01)
*A61M 11/00*   (2006.01)
(Continued)

(52) U.S. Cl.
CPC ........... *A24F 47/008* (2013.01); *A61M 11/00* (2013.01); *A61M 15/0068* (2014.02);
(Continued)

(58) Field of Classification Search
CPC .................................................. A24F 47/008
See application file for complete search history.

(56) References Cited

U.S. PATENT DOCUMENTS

| 2013/0220315 A1 | 8/2013 | Conley et al. |
| 2015/0040925 A1 | 2/2015 | Saleem et al. |

(Continued)

FOREIGN PATENT DOCUMENTS

| CN | 2057059 U | 5/1990 |
| CN | 2293204 Y | 10/1998 |

(Continued)

OTHER PUBLICATIONS

International Search Report and Written Opinion for PCT/IB2016/053403, dated Aug. 3, 2016, by the European Patent Office, 10 pgs.

(Continued)

*Primary Examiner* — James Harvey
(74) *Attorney, Agent, or Firm* — Mueting, Raasch & Gebhardt, P.A.

(57) ABSTRACT

A smoking article includes a housing having a mouthpiece and configured to receive a nicotine-containing aerosol generating substance. The smoking article also includes control electronics configured to control delivery of an amount of nicotine-containing aerosol from the nicotine-containing aerosol generating substrate through the mouthpiece. The smoking article further includes a nicotine metabolite sensor positioned at the mouth piece and operably coupled to the control electronics. The sensor is positioned such that when a smoker places their lips in contact with the mouthpiece the sensor can detect an amount or concentration of a nicotine metabolite in the smoker's saliva. The smoking article can store or report data regarding the amount of nicotine metabolite detected by the sensor to, for example, the smoker. In addition or alternatively, the control electronics can receive data from the sensor to control whether the amount of the nicotine-containing aerosol is delivered.

15 Claims, 4 Drawing Sheets

(51) Int. Cl.
*A61M 15/00* (2006.01)
*G01N 27/416* (2006.01)
*H05B 1/02* (2006.01)
*A61B 5/145* (2006.01)

(52) U.S. Cl.
CPC ......... *G01N 27/416* (2013.01); *H05B 1/0297* (2013.01); *A61B 5/14507* (2013.01); *A61B 5/14546* (2013.01)

(56) References Cited

U.S. PATENT DOCUMENTS

| | | | |
|---|---|---|---|
| 2018/0140016 A1* | 5/2018 | Thorens | A24F 47/008 |
| 2018/0146708 A1* | 5/2018 | Batista | A24F 47/008 |
| 2019/0053538 A1* | 2/2019 | Batista | A24F 47/008 |

FOREIGN PATENT DOCUMENTS

| | | |
|---|---|---|
| CN | 101583354 A | 11/2009 |
| CN | 201781979 U | 4/2011 |
| CN | 202 133 664 U | 2/2012 |
| CN | 102573821 A | 7/2012 |
| CN | 103 783 669 A | 5/2014 |
| CN | 104256895 A | 1/2015 |
| CN | 104267140 A | 1/2015 |
| CN | 204070558 U | 1/2015 |
| RU | 2009138240 A | 4/2011 |
| RU | 2424750 C2 | 7/2011 |
| WO | WO 2010/003480 A1 | 1/2010 |
| WO | WO 2011/141712 A1 | 11/2011 |
| WO | WO 2013/098398 A2 | 7/2013 |

OTHER PUBLICATIONS

International Preliminary Report on Patentability for PCT/IB2016/053403, dated May 19, 2017, by the European Patent Office, 11 pgs.
European Search Report for EP 15171992.9, issued by the European Patent Office dated Aug. 19, 2015; 5 pgs.
Britton et al., "Comparison of Self-Reported Smoking and Urinary Cotinine Levels in a Rural Pregnant Population," *Journal of Obstetric, Gynecologic, & Neonatal Nursing*, May 2004, 33(3), 306-311.
Collins et al., "Toxicology. Transforming environmental health protection," *Science*, Feb. 15, 2008, 319(5865): 906-907.
Etzel RA, "A review of the use of saliva cotinine as a marker of tobacco smoke exposure," *Prey Med.*, Mar. 1990; 19(2):190-7.
Figueiredo et al., "Determinants of salivary cotinine level: a population-based study in Brazil," *Rev Saude Publica.*, Dec. 2007;41(6):954-962.
Gorber et al., "The accuracy of self-reported smoking: A systematic review of the relationship between self-reported and cotinine-assessed smoking status," *Nicotine & Tobacco Research*, Jan. 1, 2009, 11(1), 12-24.
Hall et al., "Blood cotinine levels as indicators of smoking treatment outcome," *Clinical Phamacology & Therapeutics*, Jun. 2, 1984, 35(6), 810-814.
Lewis et al., "Cotinine Levels and Self-Reported Smoking Status in Patients attending a bronchoscopy clinic," *Biomarkers*, 2003, 8(3-4), 218-228.
Pettiti et al., "Accuracy of Information on Smoking Habits Provided on Self-Administered Research Questionnaires," *American Journal of Public Health*, Mar. 1981, 71(3), 308-311.
Ricci et al., "A Review of experimental aspects of electrochemical immunosensors," *Electrochimica Acta*, Dec. 1, 2012;84:74-83.
Studts et al., "Validity of Self-Reported Smoking Status among Participants in a lung Cancer Screening Trial," *Cancer Epidemiology Biomarkers & Prevention*, Oct. 2006, 15(10), 1825-1828.
*Toxicity Testing in the 21st Century: A Vision and a Strategy*; The National Academies Press: Washington, DC, USA, 2007. Cover page, title page and table of contents.
Vogt et al., "Comparison of biochemical and questionnaire estimates of tobacco exposure," *Preventive Medicine*, Jan. 1979, 8(1), 23-33.
Yuki et al., "Good relationship between saliva cotinine kinetics and plasma cotinine kinetics after smoking one cigarette," *Regul Toxicol Pharmacol*. Nov. 2013;67(2):240-5. doi: 10.1016/j.yrtph.2013.08.002. Epub Aug. 8, 2013.
Russian Office Action dated Oct. 9, 2019 for corresponding RU Application No. 2017134726, issued by the Patent office of the Russian Federation; 13 pgs. Including English translation.
Chinese Office Action dated Nov. 14, 2019 for corresponding CN Application No. 201680029298.6, issued by the China National Intellectual Property Administration; 17 pgs. Including English translation.

* cited by examiner

BIOLOGICAL CONTROL IN ELECTRONIC SMOKING ARTICLES

CROSS-REFERENCE RELATED APPLICATIONS

This application is the § 371 U.S. National Stage of International Application No. PCT/IB2016/053403, filed 9 Jun. 2016, which claims the benefit of EP Patent Application No. 15171992.9, filed 12 Jun. 2015.

FIELD OF INVENTION

This disclosure relates to, among other things, electronic smoking articles that include a nicotine metabolite sensor. The nicotine metabolite sensor can be coupled to electronics of the smoking article to provide feedback to a smoker, to prevent delivery of a nicotine-containing aerosol, if appropriate, and the like. Quantities of the nicotine metabolite can preferably be related to nicotine exposure levels of a smoker.

BACKGROUND

Nicotine dose control presents challenges in the development of electronic smoking articles configured to deliver an aerosol containing nicotine. Smokers have been observed to alter their smoking patterns to receive higher doses of nicotine when smoking low nicotine delivery products such as certain electronic smoking articles. Compensatory changes in smoking behaviour include taking larger puff volumes, more frequent puffs, inhaling more deeply, blocking ventilation, or taking more puffs per day.

Most nicotine dose control technology employed in electronic smoking articles is based on controlling the amount of nicotine-containing aerosol delivered within an individual puff and does not, for example, count for the frequency of repeated puffs. The mechanism for control depends on the type of electronic smoking article used. By way of example, existing control mechanism include controlling the energy supplied to heat a nicotine-containing aerosol generating substrate or controlling valve actuation sequence to deliver a pressurized source of a nicotine-containing composition. Such technology is configured to control the dose delivered by the smoking article and is not based on the parameters associated with the smoker, which can vary substantially between individuals.

SUMMARY

In one aspect of the present invention, a smoking article includes a housing having a mouthpiece and configured to receive a nicotine-containing aerosol generating substance. The smoking article also includes control electronics configured to control delivery of an amount of nicotine-containing aerosol from the nicotine-containing aerosol generating substrate through the mouthpiece. The smoking article further includes a nicotine metabolite sensor positioned at the mouth piece and operably coupled to the control electronics. The sensor is positioned such that when or after a smoker places their lips in contact with the mouthpiece the sensor can detect an amount or concentration of a nicotine metabolite in the smoker's saliva. The smoking article can store or report data regarding the amount of nicotine metabolite detected by the sensor to, for example, the smoker. In addition or alternatively, the control electronics can receive data from the sensor to control whether the amount of the nicotine-containing aerosol is delivered.

Thus examples of the present invention can provide a smoking article that monitors an effect of smoking on a smoker and provides feedback to the smoker based on the monitored effect. The smoking article can in some examples monitor an effect of smoking on a smoker and can control the output of the smoking article based on the monitored effect. Such monitoring of the effect of smoking on the smoker, rather than monitoring the amount of a substance delivered by a smoking article to the smoker can give a more accurate indication in some cases of the effect on the user, for example where the user uses more than one smoking device or for example mixes use of an electronic smoking device with the smoking of combustible cigarettes.

Example devices of the present invention can also prevent or restrict smoking of the device including nicotine-containing substrates by non-smokers or non-adult users. Other advantages of examples of the present invention will be evident to those of skill in the art upon reading and understanding the present disclosure, which includes the claims that follow and the accompanying drawings.

Various aspects of the present invention may have one or more advantages relative to currently available or previously described electronic smoking articles. For example, the electronic smoking articles described herein can provide information to the smoker or the smoking article that is more relevant to the individual smoker than is possible with other smoking articles. Nicotine dosing and summing systems in currently available or proposed electronic smoking articles take into account the dose delivered by the device to the smoker, but do not account for individual smoking behaviours or other individual parameters such as metabolism associated with, for example, weight, ethnicity and gender of the smoker, which can result in substantial differences between individual smokers. By determining nicotine metabolite concentrations of the individual smoker, such differences are automatically taken into account. By providing an assay that measures an effect of smoking on an individual smoker, as opposed to an assay that measures a dose delivered to the smoker, more meaningful information regarding the individual smoker can be obtained and used as desired. These and other advantages of various aspects of the present invention will be evident to those of skill in the art upon reading and understanding the present disclosure.

The present invention is applicable to any suitable electronic smoking article. Any electronic smoking article that includes a mouthpiece configured to contact a smoker's lips can be used or modified in accordance with the present invention. As used herein, a "smoking article" is an article that is configured to deliver an aerosol to a smoker using the article. For purposes of the present invention, the smoking article includes a one-part or multiple-part housing having a mouthpiece and configured to receive a nicotine-containing aerosol generating substrate. The substrate can be in any suitable form. For example, the substrate can include tobacco. In some embodiments, the substrate includes a liquid composition comprising nicotine. In some embodiments, the substrate comprises a dry powder containing nicotine, such as a nicotine salt. A "smoking article" includes articles that heat, directly or indirectly, the nicotine-containing aerosol generating substrate to produce the nicotine-containing aerosol and articles that do not heat the substrate but rather use air flow or a chemical reaction to deliver nicotine-containing aerosol.

As used herein, an "electronic smoking article" is a smoking article that has one or more electrical components that control an amount of aerosol delivered from the substrate to the smoker via the mouthpiece. The electrical components can include a substrate heater, which can include, for example, one or more electrically resistive elements or can include an electrically controllable valve positioned and configured to allow or prevent passage of an aerosol generated from the substrate to a smoker via the mouthpiece. Control of a heater, a valve or other electrical component can be accomplished by control electronics. Control electronics can be provided in any suitable form and may, for example, include a controller or a memory and a controller. The controller can include one or more of an Application Specific Integrated Circuit (ASIC) state machine, a digital signal processor, a gate array, a microprocessor, or equivalent discrete or integrated logic circuitry. Functions attributable to a controller in this disclosure can be embodied as one or more of software, firmware, and hardware.

It will be appreciated that a smoking article that does not include control electronics can be readily modified to incorporate control electronics, such as a controllable valve, to carry out one or more embodiments of the present invention.

Regardless of the type of electronic smoking article, a nicotine metabolite sensor can be placed relative to the mouthpiece such that placement of a smoker's lips on the mouthpiece will transfer saliva to the sensor so that the sensor can detect the nicotine metabolite in the saliva.

Any one or more sensors may be positioned and configured to detect any one or more nicotine metabolite in saliva upon contact of the mouthpiece with the smoker's lips. Examples of nicotine metabolites include nicotine glucuronide, nicotine N'-oxide, nicotine isomethonium ion, cotinine methonium ion, cotinine glucuronide, 3-pyridylacetic acid, nicotine-A iminium ion, cotinine, cotinine N-oxide, 4-(3-pyridyl)-butanoic acid, 2;-hydroxynicotine, nornicotine, N'-Hydroxymethyl nornicotine, 5'-hydroxycotinine, Trans-3'-hydroxycotinine, 4-(methylamino)-1-(3-pyridyl)-1-butanone, 4-oxo-4-(3-pyridyl)-butanamide, 4-oxo-4-(3-pyridyl)-N-methylbutanamide, trans-3'-hydroxycotinine glucuronide, 4-(3-pyridyl)-3-butenoic acid, 4-hydroxy-4-(3-pyridyl)-butanoic acid, 4-oxo-4-(3-pyridyl)-butanoic acid, and 5-(-3-pyridyl)-tetrahydro-furan-2-one. Preferably, at least one sensor is configured to detect cotinine levels.

Cotinine is a preferred metabolite in part because it has a long plasma-half life and because a high percentage of nicotine is converted to cotinine. For example, cotinine typically has a plasma half-life of from about 11 hours to about 37 hours, compared with about 30 minutes for nicotine. In addition, about 70% to about 80% of nicotine is converted to cotinine in the liver and delivered to the blood stream. Further, saliva concentrations of cotinine are thought to be proportional to plasma cotinine concentrations.

Preferably, a sensor is configured to quantify an amount of cotinine within a relevant range of concentrations. By way of example, studies have shown that passive exposure to cigarette smoke typically results in cotinine concentrations in saliva of below 5 ng/ml, but heavy passive exposure can results in concentrations in saliva of 10 ng/ml or greater. Saliva concentrations in saliva of infrequent cigarette smokers or in regular smokers who smoke low nicotine cigarettes may range from about 10 ng/ml to about 100 ng/ml. Regular active smokers could possibly have saliva cotinine concentrations greater than 100 ng/ml. Accordingly and preferably, the sensor is configured to accurately quantify saliva concentrations of cotinine in a range from about 5 ng/ml to about 200 ng/ml, such as from about 10 mg/ml to about 150 ng/ml. However, it will be appreciated that the range of reliability and sensitivity of the sensor may be tuned to include other concentration ranges as appropriate or desired.

An electronic smoking article of the present invention can employ any suitable sensor configured to detect cotinine in saliva. The sensor may employ any suitable cotinine detection technology. Known technologies for detecting saliva cotinine concentrations include colorimetric methods, gas chromatography (GC), GS-mass spectrometry (GC-MS), high-performance liquid chromatography (HPLC), and radioimmunoassay (RAI). NicAlert™ test strips, which are a lateral flow point of contact chromographic saliva cotinine detection system, have been developed. Such cotinine detection technologies or other suitable technologies can be adapted for use in the present invention.

In preferred embodiments, a cotinine sensor is an electrochemical sensor. Any suitable electrochemical sensor can be employed. Preferably, the sensor includes a cotinine-sensitive layer or coating disposed on a transducer, where selective binding of cotinine to the layer or coating is translated to a signal or change in signal by the transducer. For example, binding of cotinine can result in a change in frequency, current or voltage, which can be correlated to an amount of cotinine present in saliva of a smoker. In some embodiments, mass change of the coating or layer results in changes in resonance frequency of the transducer, which translates into a proportional electrical signal.

As an example the sensor can be made of a core microfluidic chip. For example, the chip may be fabricated using polydimethylsiloxane (PDMS) with standard soft lithography. Alternatively, it could be for example be adsorbed on a gold piezoelectrode via amide bonds, or a screen-printed dual carbon electrode.

Examples of coatings or layers that can be disposed on a transducer for detecting cotinine include immobilized antibodies or molecules binding specifically to the nicotine metabolite. Preferably, the sensor includes an immobilized anti-cotinine antibody or cotinine binding fragment thereof.

Currently available microfluidic immunoassay techniques that may employ, for example, as little as 10 microliters of saliva sample should be capable of linear detection of nicotine metabolites, such as cotinine, in a range from about 1 ng to about 250 ng, which is in a range that should readily allow for differentiation between a non-smoker and a heavy smoker.

A signal produced by binding of cotinine to a coating or layer of a sensor can be amplified in any suitable manner to increase the speed or sensitivity of the sensor. For example, enzyme amplification, such as horseradish peroxidase-based amplification, can be employed. Preferably, the amplification enzyme is stored in proximity to the sensor and can migrate when wetted by saliva to interact with the sensor. Preferably, a substrate for the enzyme is stored in proximity to the sensor and can migrate when wetted by saliva to interact with the sensor. The substrate or the amplification enzyme can be stored in a vehicle to prevent interaction, and thus depletion of the substrate, prior to wetting by saliva. Preferably, the vehicle is configured to allow release of the substrate or the amplification enzyme when contacted with saliva. In some embodiments, the substrate and the amplification enzyme are separately stored in vehicles. For example, the substrate or the enzyme can be encapsulated in liposomes, or the substrate and the enzyme can be separately encapsulated in liposomes.

In some embodiments, a secondary cotinine binding partner, such as an anti-cotinine antibody or antibody fragment, is conjugated to the amplification enzyme. If cotinine is present in saliva and is bound to the coating or layer of the sensor, the secondary antibody can bind to the immobilized cotinine to immobilize the enzyme. Accumulation of a detectable species, resulting from the enzyme-catalysed conversion of the substrate, thus can occur in proximity to the sensor.

Enzyme-substrate pairs can be selected based on the type of sensor employed. For example, if the sensor responds to mass accumulated on the sensor, enzyme conversion of the substrate can result in a species that precipitates on the sensor or that binds to the sensor or a coating thereof. By way of another example, enzyme conversion of the substrate can result in a species of a different charge, as appropriate, based on the sensor.

In some embodiments, the sensor is a positive potential barrier sensory film and is configured to measure charge density distribution. In some embodiments, the sensor is configured to measure electrochemical impedance to determine nicotine metabolite concentration.

In some embodiments, the cotinine sensor is an RFID tag sensor that includes an RFID tag and a cotinine-sensitive coating operably coupled to the RFID tag. RFID sensors can advantageously be passive, requiring no battery power to be used by the sensor. An RFID sensor can be interrogated by a powered RFID reader as known in the art. In many embodiments, a resonance frequency of the RFID sensor changes as differing amounts of cotinine bind to the coating. The RFID reader can sweep the sensor to determine the resonance frequency of the tag, which can correlate to the amount of cotinine present. The RFID reader can, in some embodiments, be configured to interrogate the RFID tag of the sensor at only one resonance frequency, such as the resonance frequency of the sensor without bound analyte or the frequency of the sensor with bound analyte. The electronic smoking article can include the RFID reader. The RFID reader can be coupled to a power supply and control electronics of the smoking article.

Preferably, a cotinine detection system of the present invention is re-usable and reliable. Preferably, the cotinine sensor allows for reliable, quantifiable, and accurate puff-by-puff analysis of cotinine concentration in a smoker's saliva.

In some embodiments, the cotinine detection system is disposable. For example, a one-use cotinine detecting mouthpiece can be employed. The mouthpiece or a portion of the mouthpiece, such as a one-use strip, can be replaced before or after a given use of an electronic smoking article. In some embodiments, the detection system can be used at the initiation of an experience with the smoking article. The experience can be defined in any suitable manner, such as a time period of 20 minutes to 60 minutes or a number of puffs, such as 10 puffs to 30 puffs. The cotinine level can be checked one or more times during the experience as appropriate. The results can be used or communicated as discussed in more detail below.

The mouthpiece can include a multilayer cover that has an outer hydrophilic, porous, or hydrophilic and porous layer to allow the capture of saliva. Preferably, the outer layer provides for capture of a predefined amount of saliva. Other layers of the mouthpiece can support the cotinine sensor.

Preferably, the sensor selectively or specifically responds to cotinine in the presence of other nicotine metabolite species or nicotine. Preferably, the sensor is sufficiently sensitive to respond quickly to a change in concentration of cotinine in saliva. Preferably, the sensor is thermodynamically reversible such that the sensor can respond to a change in cotinine concentration without an accumulation effect, such as memory or hysteresis effects. Preferably, the sensor's limit of detection corresponds to a signal standard deviation to background noise ratio below 3 for the cotinine analyte.

Sensor technology that can be employed to achieve or approach such results is described by, for example, Francesco Riccia, b, Gianluca Adornettoa, Giuseppe Palleschia, ELECTROCHEMICAL SCIENCE AND TECHNOLOGY State of the Art and Future Perspectives On the occasion of the International Year of Chemistry (2011); Electrochimica Acta; Volume 84, 1 Dec. 2012, Pages 74-83, which is incorporated herein by reference in its entirety to the extent that it does not conflict with the present disclosure.

It will be appreciated that a sensor for detecting nicotine metabolites other than cotinine can employ similar technology to that discussed above with regard to cotinine and that cotinine sensors are discussed herein for purposes of example and illustration.

Regardless of the nicotine metabolite detected, nicotine metabolite data obtained by a smoking article of the present invention can be used for any one or more suitable purpose, only a few of which are described in the present disclosure in more detail.

In preferred embodiments, a smoking article includes a nicotine metabolite sensor operably coupled to control electronics to prevent the article from delivering an amount of a nicotine-containing aerosol if a concentration or amount of the metabolite is below a predetermined minimum threshold. In such embodiments, accidental or unwanted use of the smoking article can be prevented. By way of example, the device can be configured to prevent non-smokers from effectively using the smoking article or from receiving a dose, or a full dose, of nicotine-containing aerosol. Because non-smokers should have little to no nicotine metabolite in their saliva, the amount of nicotine metabolite detected by the sensor when the non-smoker places their lips on the mouthpiece should be below the predetermined minimum threshold. If the minimum threshold is not met, control electronics of the device can prevent an amount of a nicotine-containing aerosol from being delivered by the smoking article. The amount of nicotine prevented from being delivered may be any portion of a full dose that the smoking article is configured to deliver. Preferably, the amount of nicotine prevented from being delivered is the full dose.

In preferred embodiments, a smoking article includes a nicotine metabolite sensor operably coupled to control electronics to prevent the article from delivering an amount of a nicotine-containing aerosol if a concentration or amount of the metabolite is above a predetermined maximum threshold. In such embodiments, delivery of nicotine to smokers having high nicotine exposure can be limited. Because frequent smokers who are exposed to large amounts of nicotine should have high amounts of nicotine metabolite in their saliva, the amount of nicotine metabolite detected by the sensor when a frequent smoker places their lips on the mouthpiece may be above the predetermined maximum threshold. The amount of nicotine prevented from being delivered may be any portion of a full dose that the smoking article is configured to deliver. Preferably, the amount of nicotine prevented from being delivered is the full dose.

The maximum threshold can be set in any suitable manner. For example, the maximum threshold can be set by a manufacturer of the smoking article, by a smoker, or by another person, such as a healthcare provider who is assisting or monitoring the smoker with regard to a smoking cessation program. Regardless of who sets the threshold or when the threshold is set, smoking articles configured to prevent further full or partial dose delivery of nicotine-containing aerosol when the maximum threshold is exceeded can be advantageously used as part of a smoking cessation program, where the maximum threshold can be reduced over time. In some embodiments where the maximum threshold can be changed over time, the smoking article preferably includes input apparatus operably coupled to the control electronics. The input apparatus can include wired or wireless communication apparatus. Wired communication apparatus include one or more ports, such as a USB port or a fire wire port, for operably coupling the smoking article to another computing apparatus, such as a smart phone or a computer.

Wireless communication apparatus include telemetry, Bluetooth, infrared, or other wireless receivers for operably coupling the smoking article to another computing apparatus, such as a smart phone or a computer. The computer, smart phone, or other computing apparatus can be used to provide instructions to the control electronics of the smoking article to set the maximum threshold to a desired value. Alternatively or in addition, the smoking article can contain a touch screen, one or more buttons, one or more dials, one or more levels, or other input apparatus operably coupled to control electronics to allow the maximum nicotine metabolite threshold to be set.

In some embodiments, the smoking article is configured to prevent an amount of a nicotine-containing aerosol from being delivered if a concentration or amount of the metabolite is above a predetermined maximum threshold at any point in time. In other embodiments, the smoking article is configured to prevent an amount of a nicotine-containing aerosol from being delivered if a concentration or amount of the metabolite detected by the sensor is above a predetermined maximum threshold for a predetermined amount of time. By preventing delivery if the threshold is exceeded for a predetermined period of time, the smoking article may reduce the likelihood of prevention of use due to artefacts, such as temporary false positive results or peaks that may occur during a puff, but which are not necessarily reflective of baseline nicotine metabolite concentrations.

In some embodiments where the smoking article is configured to prevent delivery of an amount of a nicotine-containing aerosol, the smoking article includes a controllable valve operably coupled to a nicotine metabolite sensor. The valve can be positioned along a flow path that extends from the nicotine-containing aerosol generating substrate to a mouth end of the mouthpiece. The valve can be configured to adapt a default configuration, such as closed, to prevent delivery of nicotine-containing aerosol to a smoker through the mouthpiece unless one or both of the minimum threshold is met and the maximum threshold is not exceeded. Alternatively, the valve can be configured to adapt a default configuration, such as open, to allow delivery of nicotine-containing aerosol to a smoker through the mouthpiece, and if a concentration or amount of a nicotine metabolite is one or both of below the minimum threshold and above the maximum threshold, the valve can adapt a configuration to prevent delivery of the aerosol.

In some embodiments where the smoking article is configured to prevent delivery of an amount of a nicotine-containing aerosol, the smoking article includes a heater configured to heat a nicotine-containing substrate to generate a nicotine-containing aerosol to be delivered to a smoker. The heater can be operably coupled to a nicotine metabolite sensor. The heater may be prevented from being activated unless a concentration or amount of a nicotine metabolite is detected by the sensor as being one or both of above the predetermined minimum threshold and below the predetermined maximum threshold. Alternatively, the heater may be configured to adapt a default configuration of being activated, and if a concentration or amount of nicotine metabolite is one or both of below the minimum threshold and above the maximum threshold, the heater can be inactivated. In such cases, some amount of nicotine-containing aerosol may be available for delivery to smoker due to prior heating of the substrate.

In some embodiments, a smoking article includes a heater configured to heat a nicotine-containing substrate to generate a nicotine-containing aerosol to be delivered to a smoker and includes a controllable valve, such as a valve as discussed above.

Alternatively or in addition to preventing an amount of nicotine-containing aerosol from being delivered from the smoking article, control electronics of the smoking article can be operably coupled to alarm apparatus to provide an alert that one or both of a minimum threshold is not met or a maximum threshold is exceed. Alarm apparatus may include, for example, apparatus that when activated cause the smoking article to vibrate, a speaker to provide an audible sound, led lights that can flash, and a display for presenting a warning. Alternatively, the alarm apparatus can be external to the smoking article and coupled to output apparatus of the smoking article. Alarm apparatus can include, for example, a smart phone.

Optionally if levels of nicotine metabolite in the smoker's saliva are detected as approaching the threshold during previous puffs, the smoking article or device operably coupled to the smoking article can provide an alert to the smoker that the maximum limit is being approached. Accordingly, more than one limit can be programmed into the smoking article to inform the smoker as the day progresses.

In some embodiments, the smoking article includes level indicators, such as bars, colours, or the like that provide the smoker with an indication of their nicotine metabolite levels relative to the threshold.

In preferred embodiments, a smoking article includes storage apparatus, such as memory, operably coupled to the sensor for storing data obtained by the sensor. In such embodiments, the smoking article preferably includes output apparatus for displaying information regarding the stored data or for transferring the stored data to another device for display, analysis or display and analysis. Output apparatus can include output communication apparatus. Output communication apparatus can be wired or wireless communication apparatus. Wired output communication apparatus can include one or more ports, such as a USB port or a fire wire port, for operably coupling the smoking article to another computing apparatus, such as a smart phone or a computer. Wireless communication apparatus include telemetry, Bluetooth, infrared, or other wireless transmitters for operably coupling the smoking article to another computing apparatus, such as a smart phone or a computer. The computer, smart phone, or other computing apparatus can be used to receive data obtained by a nicotine metabolite sensor. The computing apparatus can then be used to analyse, display, or analyse and display the sensed data. Alternatively or in addition, the smoking article can include a display to provide the user with information regarding data obtained by a nicotine metabolite sensor. Regardless of how information regarding data obtained by a nicotine metabolite sensor is displayed, the displayed information can be advantageously used by a smoker or another person, such as a healthcare provider, assisting or monitoring the smoker with regard to a smoking cessation program.

In some embodiments, a smoking article includes output apparatus for real-time output of data obtained from a sensor but does not include storage apparatus for storing data obtained by the sensor.

The sensor can optionally be operably coupled to a puff detection apparatus to activate the sensor when a puff is detected. Such an arrangement can result in reduced power requirements of the sensor and the smoking article. Any suitable puff detection apparatus can be employed. Examples of suitable puff detection apparatus include a microphone or a thermocouple. Examples of suitable puff detection apparatus that can be included in a smoking article according to the present invention are described in, for example WO 2013/098398 and WO 2010/003480.

It will be understood that the preferred embodiments described herein can be combined in any suitable manner. For example, a smoking device configured to prevent delivery of an amount of a nicotine-containing aerosol when a minimum threshold is not met can also be configured to one or both of (i) prevent delivery of an amount of a nicotine-containing aerosol when a maximum threshold is exceed, and (ii) one or more of store, display and output information regarding data obtained by a nicotine metabolite sensor. Similarly, a smoking article that is configure to one or more of store, display and output information regarding data obtained by a nicotine metabolite sensor can also be configured to one or both of (i) prevent delivery of an amount of a nicotine-containing aerosol when a minimum threshold is not met, and (ii) prevent delivery of an amount of a nicotine-containing aerosol when a maximum threshold is exceeded. Similarly, a smoking article that is configured to prevent delivery of an amount of a nicotine-containing aerosol when a maximum threshold is exceeded can also be configured to one or both of (i) prevent delivery of an amount of a nicotine-containing aerosol when a minimum threshold is not met, and (ii) one or more of store, display and output information regarding data obtained by a nicotine metabolite sensor.

All scientific and technical terms used herein have meanings commonly used in the art unless otherwise specified. The definitions provided herein are to facilitate understanding of certain terms used frequently herein.

As used herein, the singular forms "a", "an", and "the" encompass embodiments having plural referents, unless the content clearly dictates otherwise.

As used herein, "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising," and the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

BRIEF DESCRIPTION OF THE DRAWINGS

Referring now to the drawings, in which some aspects of the present invention are illustrated. It will be understood that other aspects not depicted in the drawings fall within the scope and spirit of the present invention. The drawings are schematic drawings and are not necessarily to scale. Like numbers used in the figures refer to like components, steps and the like. However, it will be understood that the use of a number to refer to a component in a given figure is not intended to limit the component in another figure labelled with the same number. In addition, the use of different numbers to refer to components in different figures is not intended to indicate that the different numbered components cannot be the same or similar to other numbered components.

DETAILED DESCRIPTION

Figure 1:
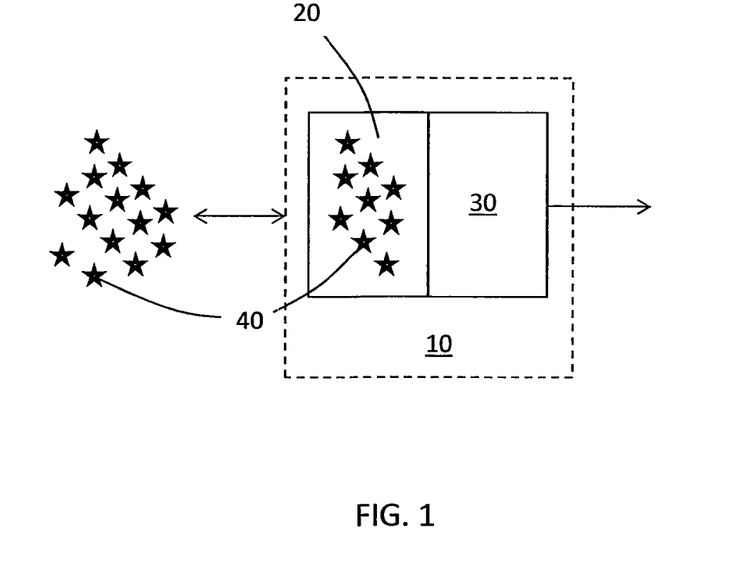
FIG. 1 is a schematic diagram depicting a nicotine metabolite electrochemical sensor and scheme for transducing a signal related to an amount or concentration of nicotine metabolite detected by the sensor.

Referring now to FIG. 1, an electrochemical nicotine metabolite sensor 10 in accordance with various aspects of the present invention can include a transducer 30 and a coating 20 or layer disposed on the transducer. The coating 20 specifically or selectively interacts with a nicotine metabolite 40 via, for example, a physiochemical reaction. The transducer 30 outputs a signal based on, for example, the mass of the metabolite 40 present in the coating 20.

Figure 2:
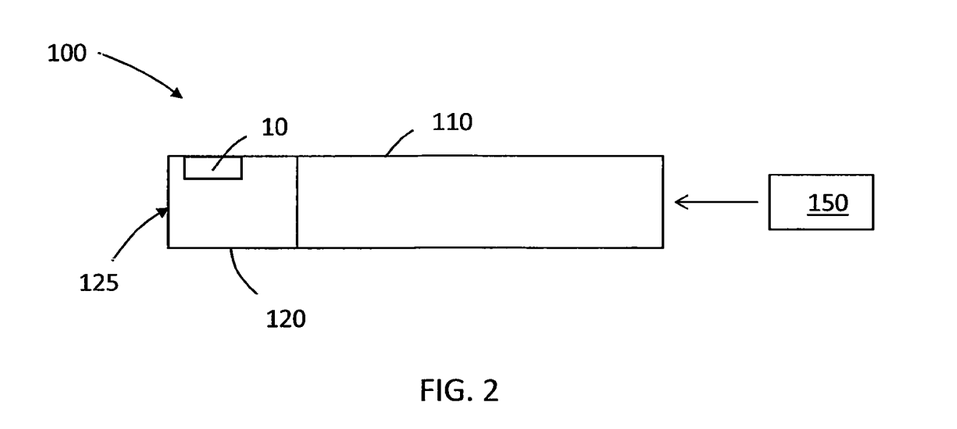
FIG. 2 is a schematic diagram of a side view of a smoking article according to various embodiments of the present invention.

Referring now to FIG. 2, a smoking article 100 in accordance with various aspects of the present invention includes a housing 110 having a mouthpiece 120 and configured to receive a nicotine-containing aerosol generating substrate 150. The mouthpiece 120 defines a mouth end 125. A nicotine metabolite sensor 10 is positioned along the mouthpiece such that when a smoker places their lips against the mouthpiece, the sensor 10 can detect an amount or concentration of nicotine metabolite in the smoker's saliva. The housing 110 may be formed of a single piece or multiple interconnected pieces. The housing 110 may be configured to receive the substrate 150 at any suitable location, including at the mouthpiece 120. One or more electrical components (not shown in FIG. 2) can be disposed in the housing 110.

Figure 3:
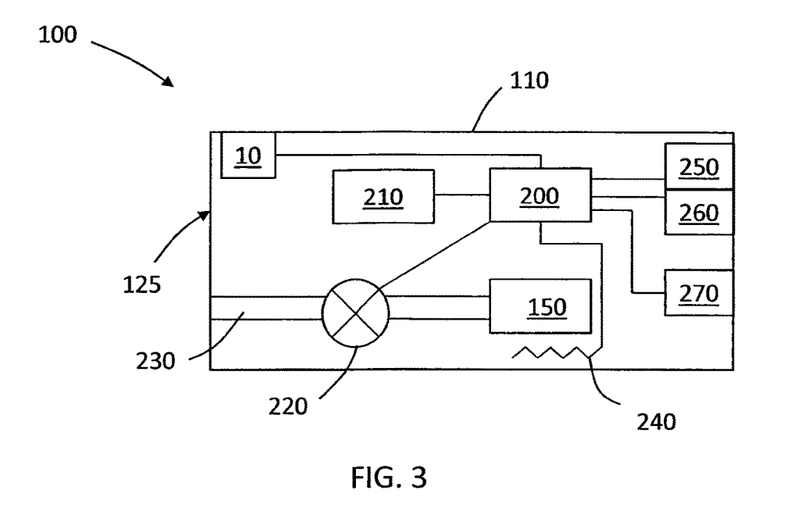
FIG. 3 is a schematic diagram illustrating some components of a smoking article according to various embodiments of the present invention.

Referring now to FIG. 3, a smoking article 100 in accordance with various aspects of the present invention includes a housing 110 configured to receive a nicotine-containing aerosol generating substrate 150. The housing 110 includes a mouth end 125. A nicotine metabolite sensor 10 is positioned in proximity to the mouth end 125. Electrical components are stored in the housing 110. The smoking article 100 includes a power source 210 operably coupled to control electronics 200. Power source 210 can be any suitable power source, such as a battery, a capacitor, or the like. Preferably, the power source 210 is a rechargeable battery, such as a rechargeable lithium ion battery, a rechargeable nickel-cadmium battery, or the like.

In the embodiment depicted in FIG. 3, the control electronics 200 are operably coupled to sensor 10, valve 220 and heater 240. Valve 220 is positioned along a pathway that extends from substrate 150 to mouth end 125 through which nicotine-containing aerosol generated by substrate can be transported. Valve 220 can adapt an open or closed configuration to allow or prevent the aerosol from traveling from substrate 150 to mouth end 125. Valve 220 can be controlled by control electronics 200 which can instruct valve whether to adapt the open or closed configuration based on data received from sensor 10.

Heater 240 is positioned in contact with or in proximity to substrate 150 and is configured to heat substrate to cause a nicotine-containing aerosol to be generated by the substrate 150. Heater 240 can be controlled by control electronics 200 so that the extent of heating of the substrate 150 can be controlled based on data received from sensor 10.

In the embodiment depicted in FIG. 3, control electronics 220 are operably coupled to input apparatus 250, output apparatus 260 and display apparatus 270.

Figure 4:
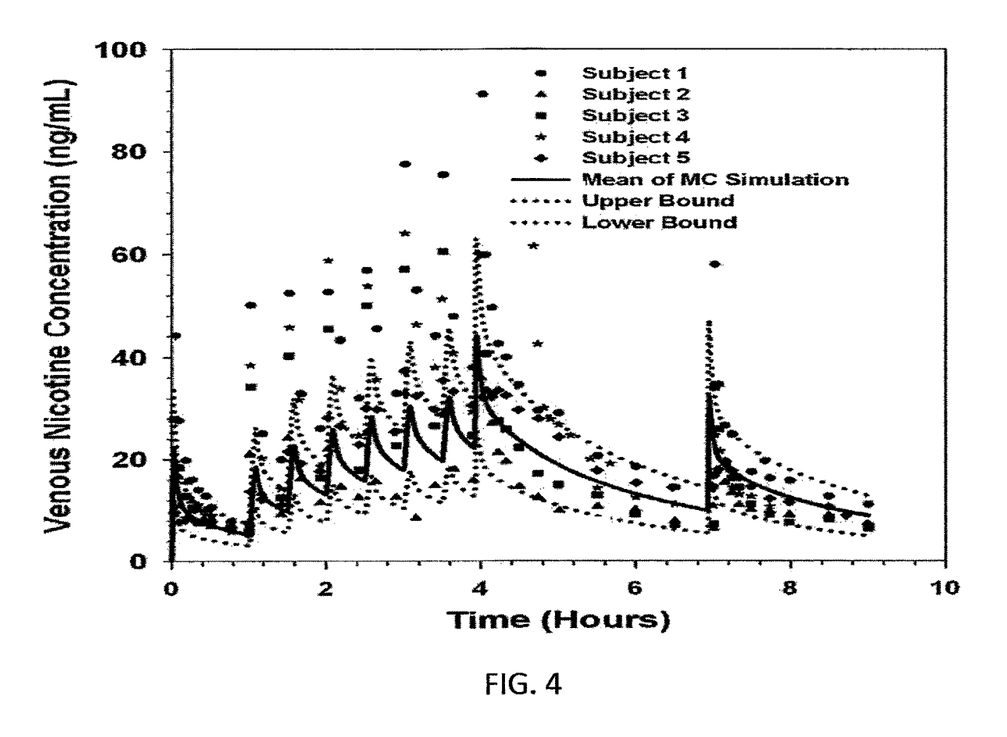
FIG. 4 is a plot of blood concentrations of nicotine in smokers over time.

Referring now to FIG. 4, the evolution of the venous nicotine concentration, which is correlated with the cotinine detection in the saliva, is depicted. FIG. 4 shows the peak increase of nicotine during the successive smoking experiences along the day, as well as the progressive increase of the baseline showing a build-up of nicotine and cotinine concentration in the body, until a starvation period; typically at night.

Figure 5:
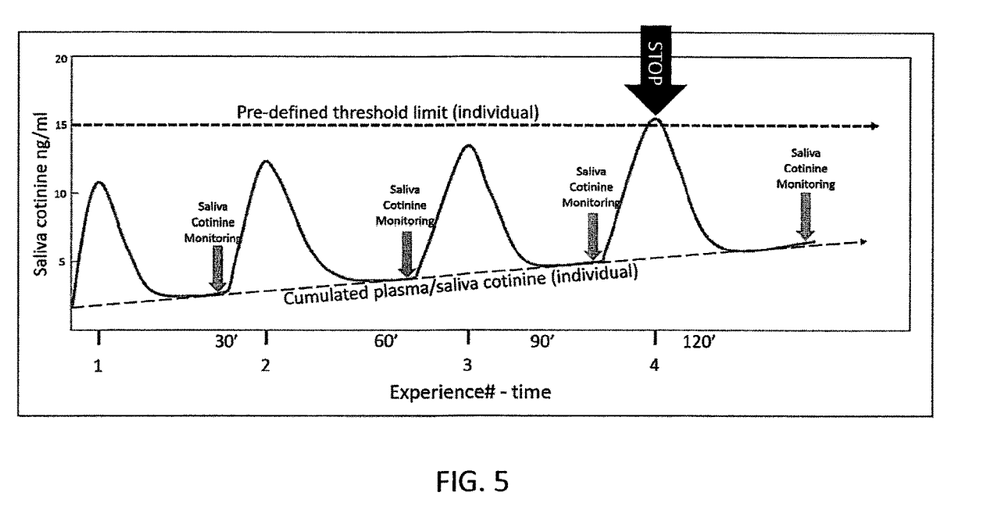
FIGS. 5-6 are schematic plots of concentrations of the nicotine metabolite, cotinine, relative to a maximum threshold over time.
Figure 6:
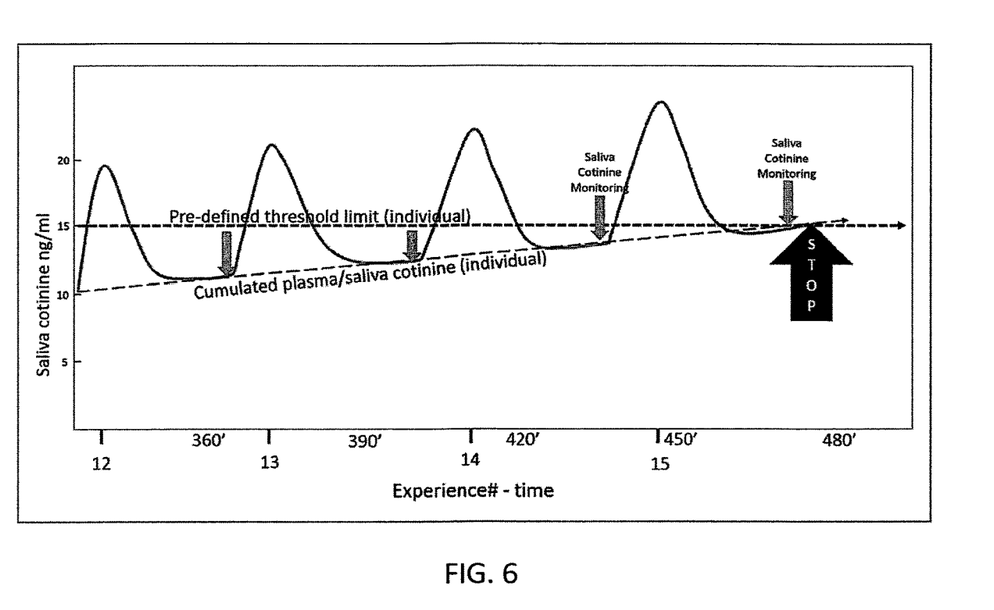

Referring now to FIGS. 5 and 6, observations from FIG. 4 are schematically depicted relative to a maximum threshold that may be permitted by a smoking article in accordance with various embodiments of the present invention. FIG. 5 schematically shows an example of a normal consumption process from the beginning of the day with the cotinine concentration increasing progressively after different smoking experiences. As depicted during the last smoking experience in FIG. 5, a peak cotinine level is detected. In some embodiments, the smoking article may be prevented from delivering an amount of nicotine-containing aerosol during the time that the threshold is exceeded. In addition or alternatively, the smoking article can provide an alarm to notify the smoker.

FIG. 6 depicts a situation where peaks during or after puffs is reached, but continued delivery of the amount of the nicotine-containing aerosol is permitted by the smoking article until the cumulative baseline cotinine levels, as opposed to temporary peaks, exceed the threshold. The temporary peaks exceeding the threshold can be ignored by, for example, requiring that the cotinine levels exceed the threshold for a predetermined amount of time, by using data collected only at the beginning of a puff or a smoking experience, or using other similar techniques. Once the cotinine level detected in the saliva reaches the threshold value, the smoking article can prevent delivery of an amount of nicotine-containing aerosol or can provide an alarm to notify the smoker.

The thresholds depicted in FIGS. 5-6 can, in preferred embodiments, be specific to the individual smoker. The thresholds can be entered into the system based on, for example, previous data acquisition or be part of a progressive cessation program, which can include decreasing the thresholds stepwise over time such as days or weeks.

Figure 7:
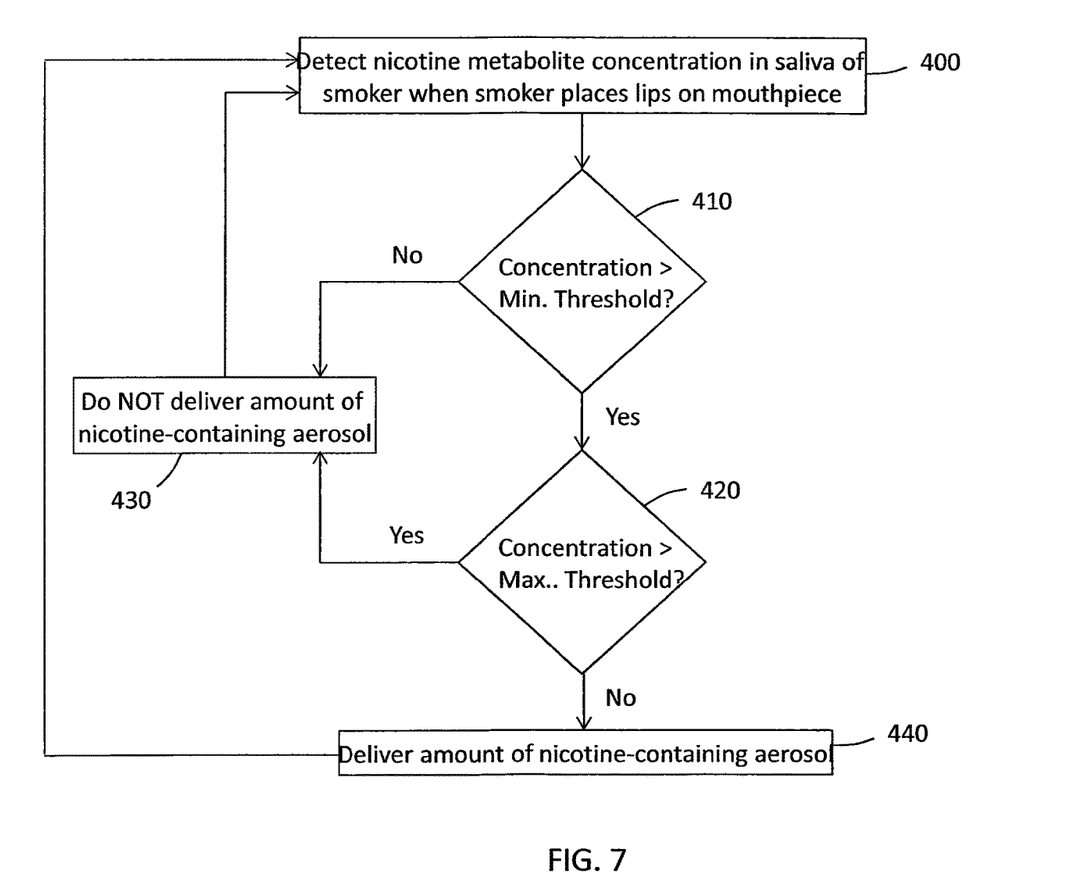
FIG. 7 is a flow chart illustrating aspects of a process that can be carried out by a smoking article in accordance with various aspects of the present invention.

Referring now to FIG. 7, a flow diagram is shown illustrating a process that can be carried out by a smoking article or system according to various embodiments of the present inventions. At step 400, a level of nicotine metabolite is detected by a sensor on a mouthpiece of a smoking article when a user places their lips on the mouthpiece. At step 410, the level of nicotine metabolite detected in step 400 is compared to a minimum threshold amount to differentiate a smoker from a non-smoker. If the level detected in step 400 is less than the minimum threshold, the smoking article will not deliver an amount of nicotine-containing aerosol (430). If the level of nicotine metabolite exceeds the minimum threshold, the level will be compared to the maximum threshold (420). If the amount exceeds the maximum threshold, the smoking article will not deliver an amount of nicotine-containing aerosol (430). However, if the level of nicotine metabolite exceeds the minimum threshold (410) but not the maximum threshold (420), the smoking article will deliver an amount of nicotine-containing aerosol (440). After an amount of nicotine-containing aerosol is delivered (440) or is not delivered (430), the process can be repeated.

As discussed above, providing an alarm is an alternative to not delivering an amount of the nicotine-containing aerosol. (430). In some embodiments, the smoking article is locked if the minimum threshold (410) is not met, but an alarm is provided if the maximum threshold is exceeded (420).

Thus, methods, systems, devices, compounds and compositions for BIOLOGICAL CONTROL IN ELECTRONIC SMOKING ARTICLES are described. Various modifications and variations of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are apparent to those skilled in electronic smoking article manufacturing or related fields are intended to be within the scope of the following claims.

The invention claimed is:

1. A smoking article comprising:
    a housing having a mouthpiece and configured to receive a nicotine-containing aerosol generating substrate;
    control electronics configured to control delivery of an amount of a nicotine-containing aerosol from the nicotine-containing aerosol generating substrate through the mouthpiece; and
    a nicotine metabolite sensor positioned at the mouthpiece and operably coupled to the control electronics.

2. The smoking article of claim 1, wherein the control electronics are configured to (i) provide an alarm, (ii) prevent delivery of the amount of the nicotine-containing aerosol, or (iii) provide an alarm and prevent delivery of the amount of the nicotine-containing aerosol, if the nicotine metabolite sensor detects an amount of nicotine metabolite below a minimum value.

3. The smoking article of claim 1, wherein the control electronics are configured to (i) provide an alarm, (ii) prevent delivery of the amount of the nicotine-containing aerosol, or (iii) provide an alarm and prevent delivery of the amount of the nicotine-containing aerosol, if the nicotine metabolite sensor detects an amount of nicotine metabolite above a maximum value.

4. The smoking article of claim 3, wherein the control electronics are configured to (i) provide an alarm, (ii) prevent delivery of the amount of the nicotine-containing aerosol, or (iii) provide an alarm and prevent delivery of the amount of the nicotine-containing aerosol, if the nicotine metabolite sensor detects an amount of nicotine metabolite above a maximum value for a predetermined amount of time.

5. The smoking article of claim 1, wherein the smoking article further comprises input apparatus operably coupled to the control electronics, wherein the input apparatus is configured to receive input relating to the maximum value from a user, and wherein control electronics are configured to receive the input and to set the maximum valve based on the input.

6. The smoking article of claim 1, wherein the nicotine metabolite sensor is configured to detect cotinine.

7. The smoking article of claim 1, further comprising a heater positioned and configured to heat the nicotine-containing aerosol generating substrate to produce the nicotine-containing aerosol.

8. The smoking article of claim 7, wherein the heater is operably coupled to the control electronics and wherein the control electronics are configured to control the extent to which the heater heats the substrate.

9. The smoking article of claim 1, wherein the control electronics include a controllable valve positioned along a flow path between a mouth end of the mouthpiece and the nicotine-containing aerosol generating substrate, wherein the valve is configured to adapt a configuration that allows flow of the nicotine-containing aerosol from the substrate to the mouth end of the mouth piece and to adapt a configuration that prevents flow of the nicotine-containing aerosol from the substrate to the mouth end of the mouth piece.

10. The smoking article of claim 1, wherein the smoking article further comprises apparatus to output data obtained by the nicotine metabolite sensor.

11. The smoking article of claim 1, further comprising storage apparatus operably coupled to the sensor to store data obtained from the sensor during use of the article.

12. The smoking article of claim 1, further comprising puff detection apparatus operably coupled to the control electronics, wherein the control electronics are configured to activate the sensor when a puff is detected by the puff detection apparatus.

13. A smoking system comprising the smoking article of claim 1, and the nicotine-containing aerosol generating substrate.

14. A smoking system according to claim 13, wherein the substrate comprises a nicotine-containing liquid composition.

15. A smoking system according to claim 13, wherein the substrate comprises a nicotine-containing dry powder.

* * * * *